(12) United States Patent
Conn et al.

(10) Patent No.: US 6,841,658 B2
(45) Date of Patent: Jan. 11, 2005

(54) PURIFICATION OF HUMAN TROPONIN I

(75) Inventors: Gregory Conn, Cary, NC (US); Brian Reardon, Cary, NC (US); Xianfang Zeng, Northborough, MA (US); Chenming Zhang, Blacksburg, VA (US)

(73) Assignee: Akzo Nobel NV, Arnheim (NL)

( * ) Notice: Subject to any disclaimer, the term of this patent is extended or adjusted under 35 U.S.C. 154(b) by 0 days.

(21) Appl. No.: 09/998,619

(22) Filed: Nov. 30, 2001

(65) Prior Publication Data

US 2002/0055145 A1 May 9, 2002

Related U.S. Application Data

(63) Continuation of application No. 09/903,398, filed on Jul. 10, 2001, now abandoned.
(60) Provisional application No. 60/217,069, filed on Jul. 10, 2000.

(51) Int. Cl.⁷ .............................. C07K 1/14; C07K 1/16; C12N 15/00
(52) U.S. Cl. ....................... 530/402; 530/412; 530/335; 435/69.1; 435/252.3; 435/320.1; 435/471; 435/476; 536/23.1; 536/23.5; 536/24.2
(58) Field of Search ................................ 530/402, 412, 530/335; 435/69.1, 252.3, 320.1, 471, 476; 536/23.1, 23.5, 24.2

(56) References Cited

U.S. PATENT DOCUMENTS

| 4,421,685 A | * | 12/1983 | Chance et al. ............ 260/112.7 |
| 4,734,362 A | * | 3/1988 | Hung et al. .................... 435/68 |
| 6,156,521 A | * | 12/2000 | Buechler et al. ............. 435/7.1 |
| 6,342,585 B1 | * | 1/2002 | Grossmann .................. 530/351 |

FOREIGN PATENT DOCUMENTS

| EP | 0 361 830 | 4/1990 | ............ C07K/3/08 |
| WO | 01 30815 | 5/2001 | ........... C07K/14/18 |

OTHER PUBLICATIONS

Al–Hillawi, E. et al. (1994) Overexpression of human cardiac troponin–I and troponin–C in *Escherichia coli* and their purification and characterisation. Two point mutations allow high–level expression of troponin–I. Eur J Biochem. vol. 225, pp. 1195–1201.*

Windholz, M. et al. eds. (1983) 1 , 4–dithiothreitol, The Merck Index, p. 493, item 3394.*
Honig, B. (1999) Protein folding: from the levinthal paradox to structure prediction. J. Mol. Biol. vol. 293, pp. 283–293.*
Grushoff, P. et al. (1975) "Purification and properties of *Streptococcal nicotinamide* adenine dinucleotide glycohydrolase" J. Bacteriol. vol. 122, pp. 599–605.*
Fujita–becker, S. et al (1993) "Reconstitution of rabbit skeletal muscle troponin from the recombinant subunits all expressed in and purified from E.coli." J. Biochem. vol. 114, pp. 438–444.*
Reiffer, S. et al. (1999) "Characterization of the cardiac holotroponin complex reconstituted from native cardiac troponin T and recombinant I and C. " Eur. J. Biochem, vol. 261, pp. 40–47.*
Pateari, R. et al. (1999) "Postetranslational deamination of proteins: the case of hemoglobin J Sardegna [$\alpha50(CD8)$ His to Asn to Asp]". Clinical chem. vol. 45, pp. 21–28.*
Ngo, J. T. et al. et al, (1994) "Computational complexity protein structure prediction, and the levinthal paradox". in "The protein folding problem and tertiary structure prediction". Page 491–495, Merz, Jr. K. et al. Eds. Birkhauser, Boston.*
Stubenrauch, K. etal "Purification of a viral coat protein by an engineered polyionic sequenec", J. Chromat. vol. 737, pp. 77–84.*
"A New Method of Human Cardiac Troponin I and Troponin T Purification" A. G. Katrukha et al., Biochemistry and Molecular Biology International, vol. 36, No. 1, May 1995, pp. 195–202.
"Study of the Reactivity of Troponin Sulfhydryl Groups" A.B. Dobrovol'skii et al., Biosis Online Database Biosciences Information Service, abstract and Biokhimiya, vol. 41, No. 6, 1976, pp. 994–999.

* cited by examiner

*Primary Examiner*—Karen Cochrane Carlson
*Assistant Examiner*—Samuel Wei Liu
(74) *Attorney, Agent, or Firm*—William P. Ramey (57) ABSTRACT

The invention is directed to methods for purifying Troponin I, particularly recombinant Tropnin I produced in a bacterial expression system. Recombinant Tropnin I can be advantageously purified after reversibly protecting the free sulfhydryl groups, e.g., by forming sulfates. In a specific example, Tropnin I reacted with sodium tetrafhionate yielded sulfitolyzed Tropnin I, which was purified by chromatography on an anion exchanger, followed by hydrophobic interaction chromatography. Facile deprotection of the sulfhydryl groups yields a highly purified product ready for refolding.

16 Claims, 11 Drawing Sheets

Conversion of cysteine to S-sulfocysteine by reaction with sodium tetrathionate and reversal by exogenous thiols

FIG. 1A

The Cleavage of disulfide bonds by sodium sulfite to form the S-sulfo derivative

A. Sulfitolyzed Troponin Lot 3L4 Standard
B. Solublized Inclusion Bodies
C. Sulfitolyzed Inclusion Bodies (AEX #1 Load)
D. Anion Exchange #1 Flowthrough
E. Anion Exchange #1 Salt Eluate
F. Anion Exchange #2 Load
G. Anion Exchange #2 Flowthrough
H. Anion Exchange #2 100 mM NaCl Eluate

FIG. 9 troponin I

LysC mapping

| # | RC | Mass | Sequence | |
|---|---|---|---|---|
| 1 | -2.1 | 707.28 | - MGDEEK | (1,6) |
| 2 | 5.2 | 1618.96 | - RNRAITARRQHLK | (7,19) |
| 3 | 30.9 | 1431.76 | - SVMLQIAATELEK | (20,32) |
| 4 | -4.8 | 1132.55 | - EESRREAEK | (33,41) |
| 5 | 48.0 | 2824.26 | - QNYLAEHCPPLHIPGSMSEVQELCK | (42,66) |
| 6 | -1.8 | 595.34 | - QLRAK | (67,71) |
| 7 | 5.1 | 903.42 | - IDAAEEEK | (72,79) |
| 8 | 10.9 | 1166.58 | - YDMEVRVQK | (80,88) |
| 9 | -9.4 | 334.19 | - TSK | (89,91) |
| 10 | 5.6 | 1005.44 | - ELEDMNQK | (92,99) |
| 11 | 13.9 | 847.49 | - LFDLRGK | (100,106) |
| 12 | -1.7 | 293.17 | - FK | (107,108) |
| 13 | 28.0 | 1896.07 | - RPPLRRVRMSADAMLK | (109,124) |
| 14 | 8.0 | 587.36 | - ALLGSK | (125,130) |
| 15 | -11.9 | 283.16 | - HK | (131,132) |
| 16 | 20.5 | 1161.60 | - VCMDLRANLK | (133,142) |
| 17 | -4.8 | 373.23 | - QVK | (143,145) |
| 18 | -9.8 | 146.11 | - K | (146,146) |
| 19 | -6.8 | 620.27 | - EDTEK | (147,151) |
| 20 | 15.7 | 1543.79 | - ERDLRDVGDWRK | (152,163) |
| 21 | -0.8 | 631.32 | - NIEEK | (164,168) |
| 22 | -4.4 | 763.36 | - SGMEGRK | (169,175) |
| 23 | -9.8 | 146.11 | - K | (176,176) |
| 24 | 7.7 | 728.27 | - MFESES | (177,182) |

PURIFICATION OF HUMAN TROPONIN I

This application is a continuation of application Ser. No. 09/903,398, filed Jul. 10, 2001 abandoned, and claims priority under 35 U.S.C. §119(e) of provisional application Serial No. 60/217,069, filed Jul. 10, 2000.

FIELD OF THE INVENTION

The present invention is directed to methods for purifying human Troponin I.

BACKGROUND OF THE INVENTION

Troponin I (TnI) is a component of a heterotrimeric complex, along with troponin C (TnC) and troponin T (TnT), involved in regulation of vertebrate striated muscle contraction (Zot and Potter, Annu. Rev. Biophys. Biophys. Chem. 1987, 16:535–559; Farah and Reinah, FASEB J. 1995, 9:755–767). Muscle contraction is triggered by the binding of $Cam^{-+}$ ions to TnC. TnT binds to tropomyosin anchoring the Tn to the muscle filament. TnI is the inhibitory subunit of the troponin complex, binding to actin-tropomyosin complexes and preventing the interaction of actin and myosin. TnI is present in muscle tissue in multiple isoforms expressed from a multi-gene family (Wu et al., DNA Seq. J. DNA Seq. Mapp. 1993, 4:113–121).

Recent investigations have demonstrated a second important biological function for TnI, the ability of the molecule to inhibit both in vitro endothelial cell survival/proliferation and inhibit in vivo angiogenesis (the growth and development of blood vessels) (Moses et al., Proc. Natl. Acad. Sci. USA 1999, 96:2645–50). TnI that inhibited endothelial cell development was isolated initially from cartilagenous tissue, and subsequent studies demonstrated anti-angiogenic activity with recombinant forms of TnI expressed in *E. coli*.

The TnI subunit is a single polypeptide with a molecular weight of 21,338. The molecule contains three cysteine residues, at positions 45, 65, and 134 (Wilkinson and Grand, Biochem J. 1975, 149:493–496). Purification processes previously developed to isolate native TnI from tissue sources or recombinant TnI require maintenance of a reducing environment throughout the purification and storage of TnI, ordinarily by the addition of dithiothreitol (DTT) to protein preparations (Potter, Methods Enzymol., 1982, 85:241–263; Jha et al., Protein Exp. Purif., 1994, 5:604–613; Al-Hillawi et al., Eur. J. Biochem., 1994, 225:1195–1201). The added DTT maintains the TnI cysteine sidechain sulfhydryls in their reduced state, preventing the formation of intra- or intermolecular disulfide bond crosslinks. Disulfide bonds between TnI cysteine sidechains are not believed to be present in the active conformation of the protein involved in regulation of muscle contraction (Kluwe et al., FEBS Lett., 1993, 323:83–88), and reductant was utilized in the isolation of active anti-angiogenic forms of TnI.

The necessity of maintaining a reducing environment in processing and storage during large scale purification of TnI for commercial use poses numerous technical difficulties and increases production cost. Thus, there is a need in the art to purify and refold Tropinin I efficiently and affordably.

SUMMARY OF THE INVENTION

The present invention provides a method of preparing Troponin I. This method comprises protecting sulfhydryl groups of reduced Troponin I, particularly recombinant TnI. In a preferred embodiment of the invention, the free sulfhydryl groups are protected by sulfitolyzation (e.g., via reaction with sodium sulfite) of Troponin I expressed in a bacterial expression system. Protection of the sulfhydryl groups during Troponin I preparation obviates the costly need for maintaining reducing conditions throughout protein preparation, purification, and storage.

In a related aspect, the present invention encompasses sulfhydryl-protected Troponin I itself, and in a preferred embodiment, the Troponin I is denatured and the sulfhydryl groups protected by sulfates.

The present invention also provides a method of purifying Troponin I, which method comprises subjecting recombinant Troponin I comprising sulfhydryl protecting groups to chromatography. In a preferred embodiment of the invention, the sulfhydryl groups are protected by sulfitolyzation. In one aspect of the invention, the Troponin I is subjected to chromatography under non-reducing conditions. In a preferred embodiment of the invention the Troponin I to be purified is expressed in a bacterial expression system such as *E. coli*. In another preferred embodiment, the chromatographic support is an anion exchange column, optionally followed by hydrophobic interaction chromatography.

These and other aspects of the invention are more fully examined in the accompanying Drawings, Detailed Description, and Example.

DETAILED DESCRIPTION

Troponin I from human cartilidge has recently been reported to possess antiangiogenic activity. In order to produce proteins to exploit the antiangiogenic properties of recombinant troponin I, we overexpressed the human skeletal troponin I Cdna in *E. coli*. Expression levels range from 2–10 mg/gram of wet cell paste. The recombinant troponin I was isolated from the lysed cells in the inclusion bodies, which were solubilized and modified by sulfitolyzation of cysteine residues to improve protein processing. The sulfitolyzed protein was purified from inclusion bodies by sequential anion exchange and hydrophobic interaction chromatography. Cysteine protecting groups could be removed by reduction prior to final protein formulation. Overall yield of troponin from the multi-step purification was greater than 50% at purity levels greater than 95%. The purified recombinant human troponin I is structurally characterized, e.g., by liquid chromatography/mass spectroscopy, peptide mapping, capillary electropherisis, SEC with laser light scattering detection and SDS-PAGE.

Figure 1A:
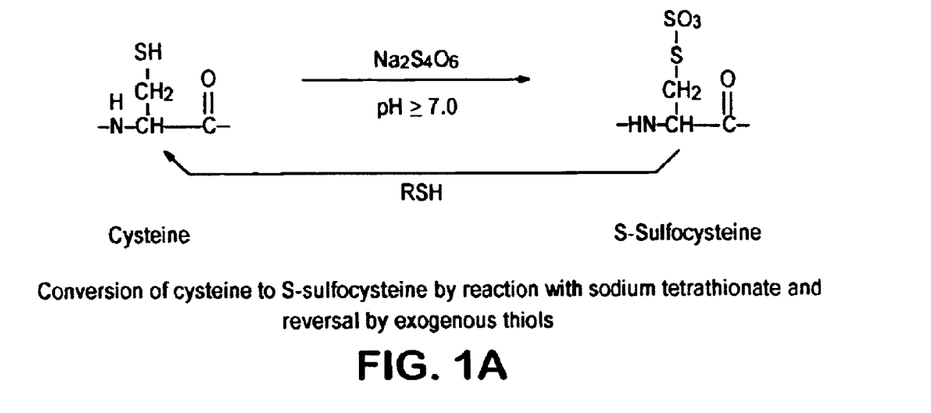
FIGS. 1A and 1B. A. Proposed reaction for oxidative sulfitolysis. B. Cleavage of disulfide bond by sodium sulfite to form the S-sulfo derivative.
Figure 1B:
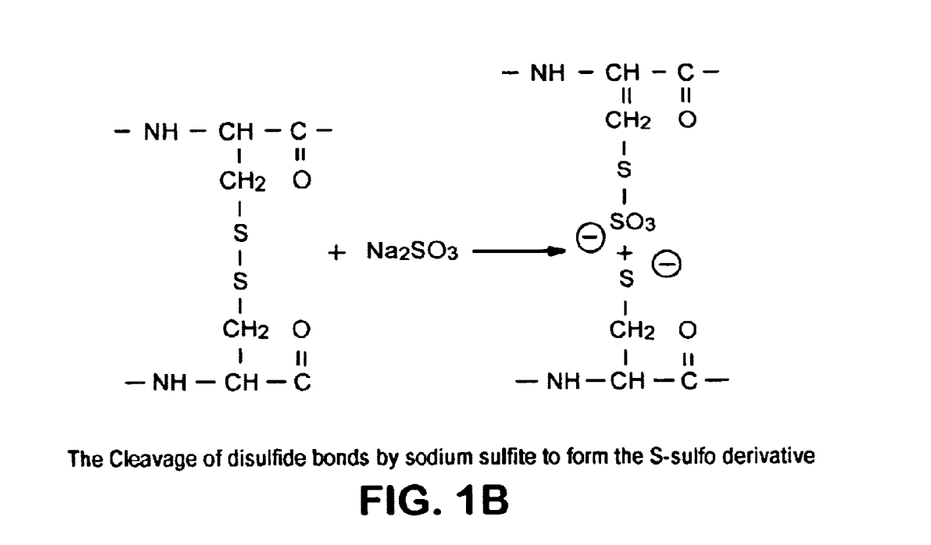

The present invention provides a method to purify and refold recombinant TnI which obviates the need for reducing agents by utilizing sulfhydryl protecting groups on the reduced protein, in particular by oxidative sulfitolysis (Chan, Biochemistry, 1968, 7(12):4247–4253) (FIG. 1). This embodiment involves an initial modification of the cysteines in troponin to yield stable S-sulfonated sidechains, which are maintained on the protein during processing and storage. The sulfate protecting groups can be removed from the TnI cysteines by treatment with a reductant to regenerate the free cysteine sulfhydryls.

The term "purified" as used herein refers to material that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Recombinant TnI can be expressed in bacterial systems in a soluable form, or an insoluable form, in inclusion bodies. Recovery of TnI from inclusion bodies requires treatment with solubilzing protein denaturants like urea. In addition, TnI, is theoretical ph is 8.8, has limited solubility at ph values above 4 in the absence of chaotropic agents, although TnI is soluble at levels of 10–20 mg/ml at low ph (less than 3). High levels (1–6 M) of the protein denaturant urea are therefore ordinarily maintained during protein purification of TnI to ensure high solubility and good protein recovery.

The term "refolding" means changes in the three-dimensional conformation of the protein, which restore the protein's biological activity, including its antiangiogenic properties.

Protein refolding of TnI into a bioactive conformation in a buffer and at a pH suitable for use in human patients requires removal of solubilizing denaturant. Circular dichroism and fluorescence studies of TnI protein folding have shown a non-linear relationship relative to chaotrope concentration in solution, with little or no apparent secondary structure at high urea concentration, and putative intermediate folded state(s) occurring between 2-4M urea (Morjana and Tal, Biotechnol. Aappl. Biochem., 1998, 28:7–17). This protein refolding process can be accomplished by dilution of TnI in a denaturant solution to an appropriate concentration, generally below 10 nanomolar, followed by removal of solubilizing chaotrope by dialysis, diafiltration, or gel filtration. Proper refolding requires appropriately timed transit through the chaotrope concentrations of 2-4M urea, where protein folding intermediates are formed, followed by a final protein concentration step.

As used herein, the term "recombinant TnI" (or troponin I) refers to TnI prepared by a biological fermentation process. TnI is a polypeptide of about 21 IkD containing three cysteine residues, although the present invention encompasses modified forms of TnI lacking one or two cysteine residues. In a specific embodiment, TnI refers to the protein described by Wilkinson and Grand (Biochem. J. 1975, 149:493–496). In a preferred embodiment, TnI of the invention lacks any disulfide bonds.

Recombinant Expression

As noted above, TnI can be prepared, albeit with certain difficulties, by fermentation of genetically modified cells. Preferably the cells are bacterial cells, which, lacking eukaryotic translational and post-translational machinery, produce improperly folded TnI that must be refolded. However, any expression system can be used to produce recombinant TnI, particularly systems that require denaturation and refolding. Furthermore, this system advantageously provides an effective technique for purifying Troponin I from any source, including natural TnI and properly folded recombinant TnI under normal purification conditions (i.e., under non-reducing conditions).

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. In a specific embodiment, the protein of interest is expressed in *E. coli* bacterial cells.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays. Host cells can be cultured cells in vitro or one or more cells in a plant, e.g., a transgenic plant or a transiently transfected plant. Host cells of the invention include, though they are not limited to, bacterial cells (e.g., *E. coli*, Synechocystis sp., *Z. mobilis, Agrobacterium tumefaciens*, and Rhodobacter); yeast cells (e.g., *S. cerevisiae, Candida utilis, Phaffia rhodozyma*); fungi (e.g., *Phycomyces blakesleeanus*); algae (e.g., *H. pluvalis*); and plants (e.g., *Arabidopsis thaliana*).

Sulfhydryl Protecting Groups

As noted above, the sensitivity of recombinant troponin to oxidation requires maintenance of reducing conditions during purification of the protein. This results in significant drawbacks in terms of expense and difficulty.

The present invention addresses these deficiencies of the prior methods by providing sulfhydryl protected recombinant troponin I.

The term "sulfhydryl protecting group" or "cysteine protecting group" means a reversibly bound chemical group which prevents formation of intra- and intermolecular disulfide bonds, but does not interfere with the process of protein purification. In a preferred embodiment, the "sulfhydryl protecting group" consists of sulfate groups bound through sufitolyzation with sodium sulfite. Numerous other reversible derivatizing reagents for cysteine sulfhydryls have been developed including disulfide compounds such as pyridyl disulfide, and the alkylalkanethiosulfonates. The sulfhydryl modification by these reagents is often facile, although their steric properties may interfere with protein activity or bioprocessing. Other sulfhydryl-reactive chemistries with potential utility in simplifying troponin I purification, recovery and storage include cyanylation and antinoethylation, reaction with compounds containing maleimide functional group such as N-ethyl maleimide, vinyl sulfones, and alkyl halides such as iodoacetic acid and amide. However, these sulfhydryl modifying groups have the disadvantage of poor reaction reversibility, making regeneration of the free sulfhydryl sidechains of the protein cysteines more difficult.

Preferably, to ensure complete protection of Troponin I's sulfhydryl groups and effective chromatographic purification, the Troponin I is denatured prior to reaction with the protecting groups under reducing conditions.

Chromatographic Methods

Anion exchange chromatography, hydrophobic interaction chromatography and preferably a combination thereof can be used to purify sulfhydryl protected TnI. Other suitable chromatographic techniques include cation exchange chromatography, gel permeation chromatography, reverse phase chromatography, metal chelation chromatography, etc. These chromatographic techniques can be employed in various formats, including high performance, preparative column, bulk suspension, and the like. In addition, the present invention is amenable to other standard laboratory or industrial separation techniques.

In a specific embodiment, sulfhydryl-protected recombinant TnI is purified by successive chromatographies on an ion exchange column, particularly an anion exchanger, followed by hydrophobic interaction chromatography.

Sulfhydryl-protected TnI can be stored in the protected state, either before or after chromatography. Storage of the sulfhydryl-protected TnI obviates the need for maintaining reducing conditions, and avoids formation of intrachain or interchain disulfide crosslinks.

The sulfhydryl-protected TnI can be deprotected after chromatographic or other purification, or storage, as set forth in the following section.

TnI Deprotection

Deprotection of the sulfhydryl protected TnI can be achieved under reducing conditions, e.g., to remove sulfate groups. The chemistries effective to remove reversible protecting groups are well-known in the art. Chemistry to remove these reversible sulfhydryl modifying groups often involves use of reductants such as mercaptans or dithiothreitol (Hoppe et al., Biochemistry 1989,28:2956; DiBella et al., J. Biol. Chem. 1995,270:163; Kenyon and Bruice, Methods Enzymol. 1977, 47:407; Bruice and Kenyon, J. Protein Chem. 1982, 1:47; Inoue et al., Biotechnol. Appl. Biochem. 1998, 28:207).

Exemplary TnI deprotection: Desulfitolyzation. Troponin may be stored or used in the sulfitolyzed form; if desulfitolyzed troponin is required the sulfhydryl group modifications may be removed by treatment of the protein with reductant such as mercaptans or dithiothreitol (DTT). At neutral to slightly acidic pH values desulfitolyzation, may be accomplished by treatment of the protein with millimolar levels of reductant (see FIG. 11) in the presence or absence of a solublizing chaotrope. In normal practice, levels 10–100 fold higher are used to ensure complete conversion of the troponin. At more acidic pH values a reductant like Tris[2-carboxyethylphosphine] hydrochloride (TCEP) is preferred. The protein may be buffer exchanged by a method such as dialysis/diafiltration or gel filtration into an acidic pH buffer prior to removal of reductant to slow the formation of intermolecular disulfides.

Protein Refolding/Formulation

Purified troponin can be refolded, if desired, by first buffer exchanging the protein by dialysis, diafiltration, gel filtration or other appropriate technique into a suitable refolding buffer in the presence of a denaturing chaotrope like 8M urea or 6M guanidine. The denatured protein may then be refolded by dilution to a suitable target concentration (e.g., less than 10 nanomolar) in an appropriate buffer with or without chaotropic agent (8–0 M urea, 6–0 M guanidine) at an appropriate temperature, and subjected to a timed hold. Alternatively, the protein may be subjected to dialysis or diafiltration through appropriate chaotrope level transitions with hold times to promote protein refolding in a suitable refolding buffer. The refolded protein is subsequently concentrated by ultrafiltration and final formulation buffer exchange, if necessary, can be accomplished by gel filtration or diafiltration.

The highly purified TnI, preferably in a refolded state, produced according to the invention can be used for any purpose, including but by no means limited to antibody generation, as a control or standard immunoassay reagent, or to inhibit angiogenesis (which can be important in treating various cancers).

EXAMPLE

The present invention will be better understood by reference to the following Example, which is provided by way of illustration and not by way of limitation.

Materials and Methods

Figure 2:
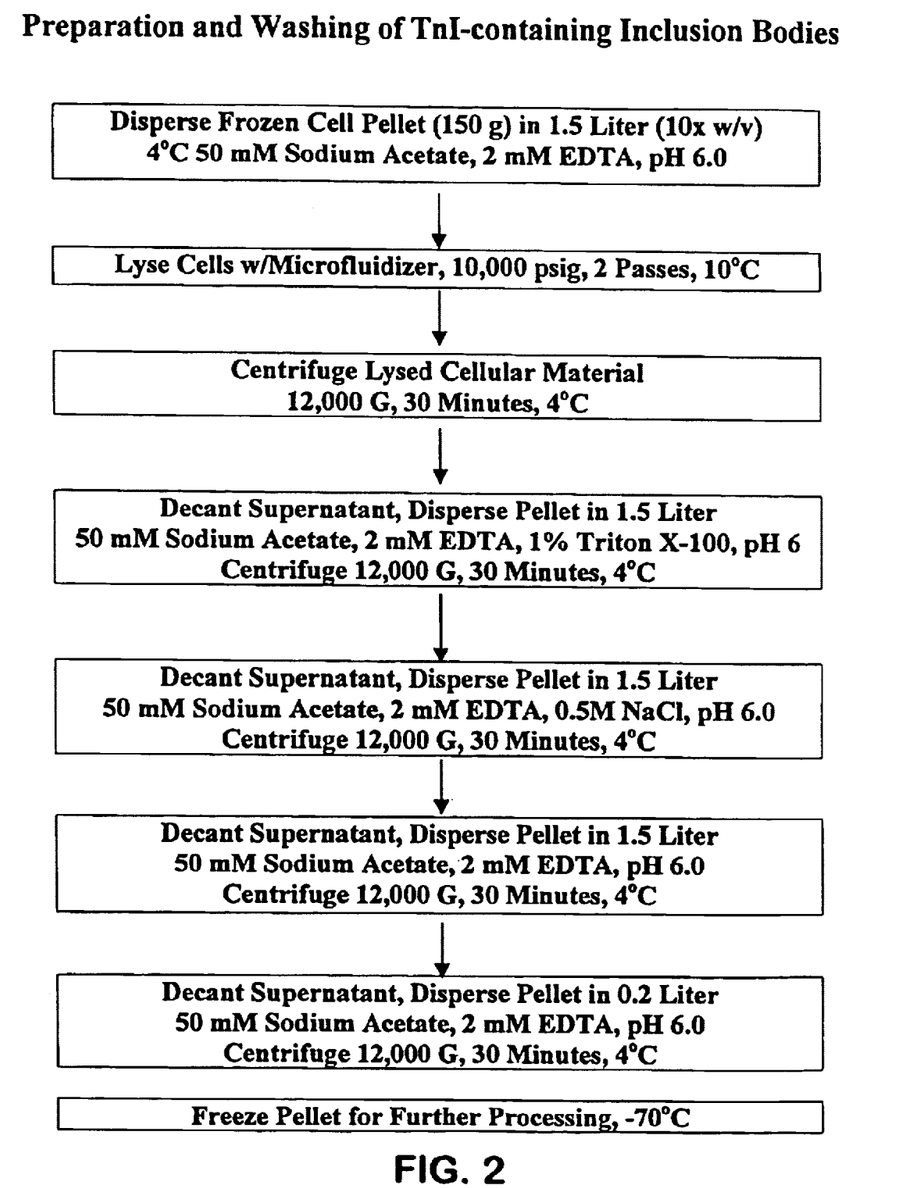
FIG. 2. Preparation and washing of TnI-containing inclusion bodies.

TnI Inclusion Body Preparation. Human skeletal TnI expressed in E. coli was isolated from lysed cells in inclusion bodies (FIG. 2). To isolate and wash inclusion bodies, approximately 150 grams of cell paste was dispersed in 1.5 liter of 50 mM sodium acetate, 2 mM EDTA, pH 6. The cell suspension is subjected to two consecutive passes through a microfluidizer, 10,000 psig at 10–12° C., to break open the cells. The resultant lysate was centrifuged at 12,000×g, 4° C. for 30 minutes to pellet insoluble material. The supernatant was removed and the pelleted material was dispersed in 1.5 liter 50 mM sodium acetate. 2 mM EDTA, 1% Triton X-100, pH 6 and centrifuged for an additional 30 minutes at 12,000×g. The pelleted material was recovered, dispersed in 1.5 liter 50 mM sodium acetate, 2 mM EDTA, 0.5M NaCl pH 6, and centrifuged for 30 minutes at 12,000 G. The pelleted material is again dispersed in 1.5 liter of 50 mM sodium acetate, 2 mM EDTA, pH 6 and centrifuged for 30 minutes at 12,000×g. The resulting pellet is suspended in 200 ml of 50 mM sodium acetate, 2 mM EDTA, pH 6 and centrifuged at 12,000 G for 30 minutes. The final pelleted inclusion bodies, approximately 10 grams, was stored at −70° C prior to subsequent processing.

Figure 3:
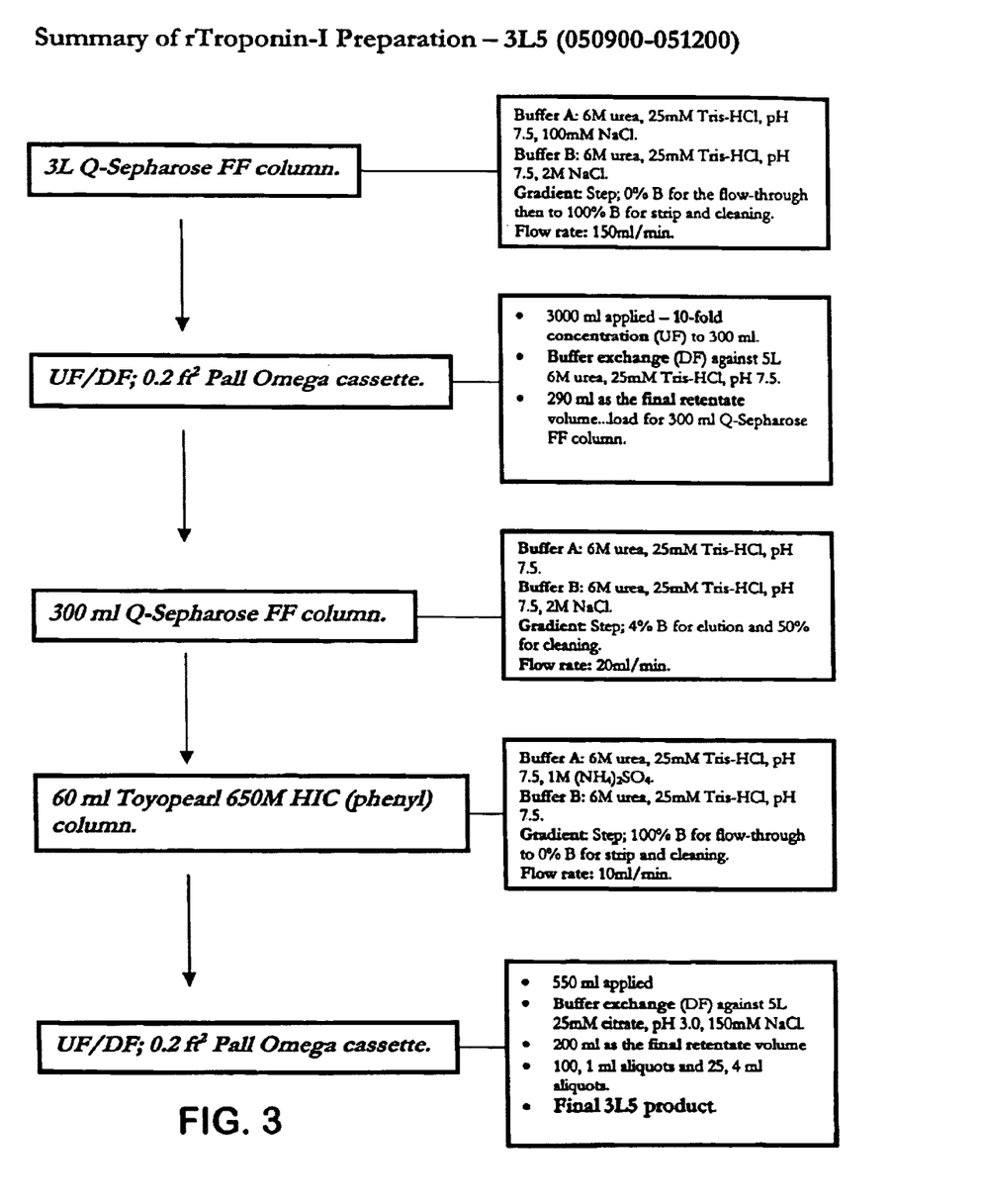
FIG. 3. Summary of recombinant Troponin preparation.

Inclusion Body Solubilization and Sulfitolyzation. Ten grams of TnI-containing inclusion bodies were solubilized and protein sulffiydryls were sulfitolyzed using 200 ml 6M urea, 25 mM Tris, 10 mg/ml sodium sulfite, 5 mg/ml sodium tetrathionate pH 7.5 at ambient temperature for 6 hours in the dark (FIG. 3). The solubilized material was filtered over a 0.2 micron membrane prior to subsequent processing.

Figure 4:
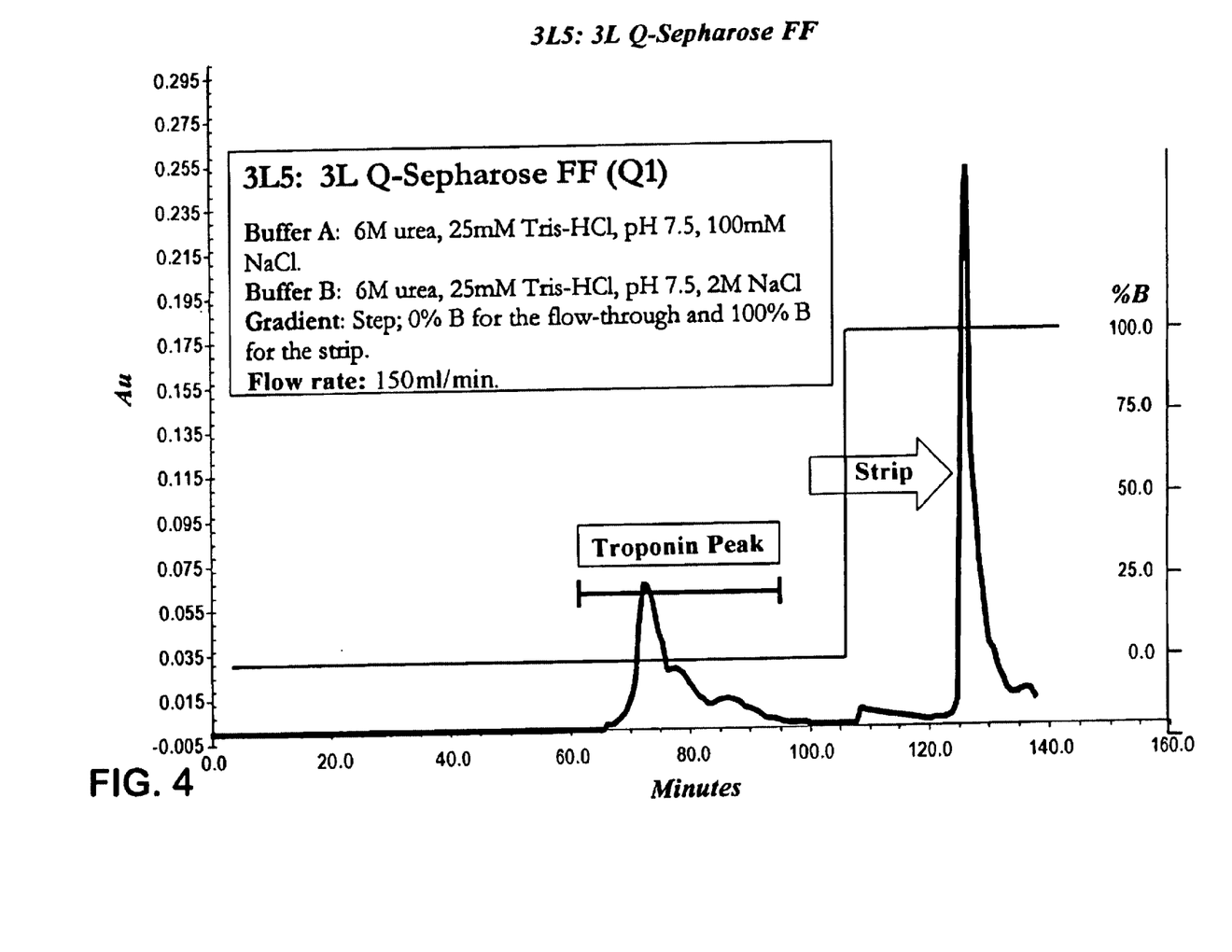
FIG. 4. Q-Sepharose FF chromatography of Troponin I. Buffer A: 6M urea, 25 mM Tris-HCl, pH 7.5, 100 mM; Buffer B: 6M urea, 25 mM Tris-HCl, pH 7.5,2M NaCl; Gradient: Step, 0% B for the flow-through and 100% B for the strip; and Flow rate: 150 ml/min.
Figure 5:
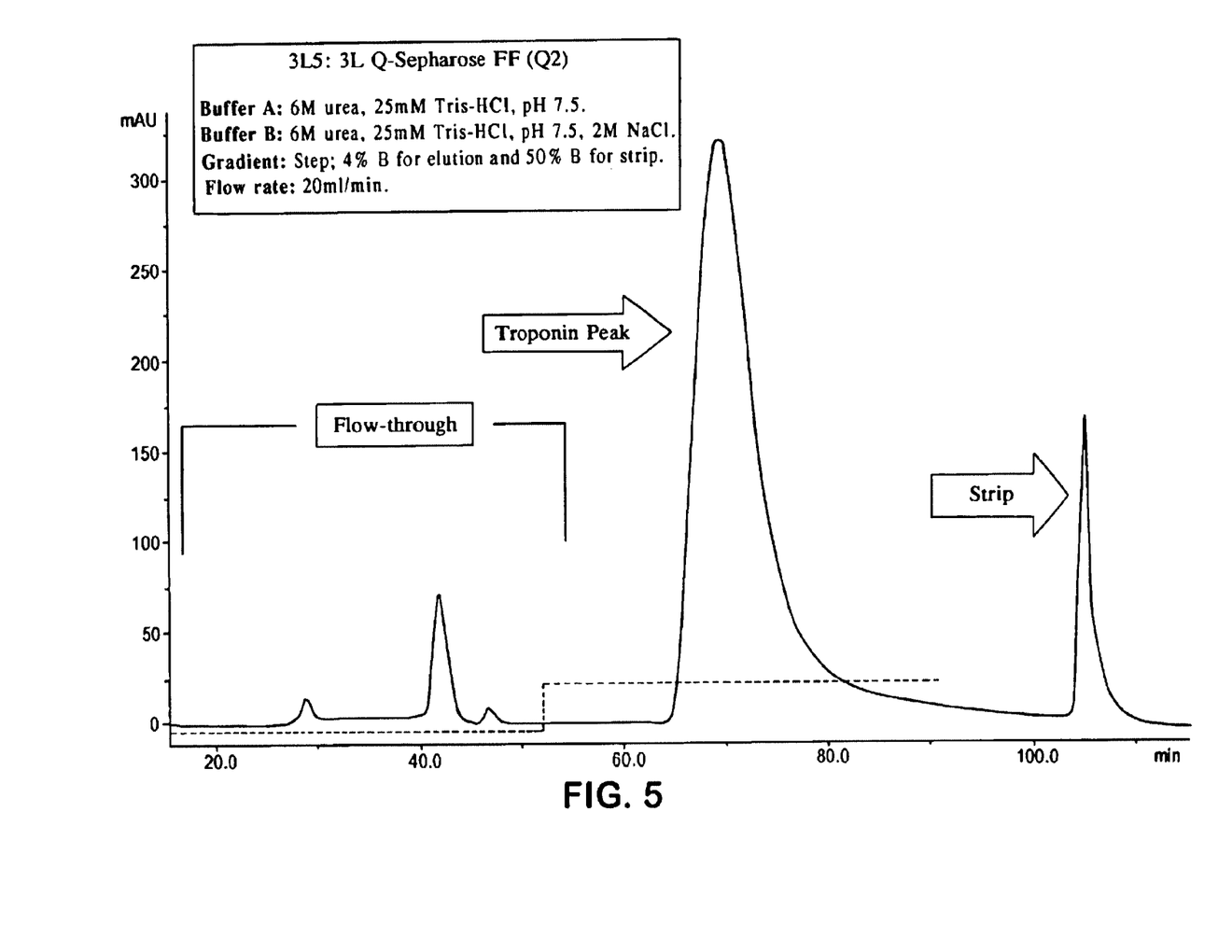
FIG. 5. 300 ml Q-sepharose FF chromatography. Buffer A: 6M urea, 25 mM Tris-HCl, pH 7.5, 100 mM; Buffer B: 6M urea, 25 mM Tris-HCl, pH 7.5, 2M NaCl; Gradient: Step, 4% B for elution and 50% B for strip; and Flow rate: 20 ml/min.
Figure 6:
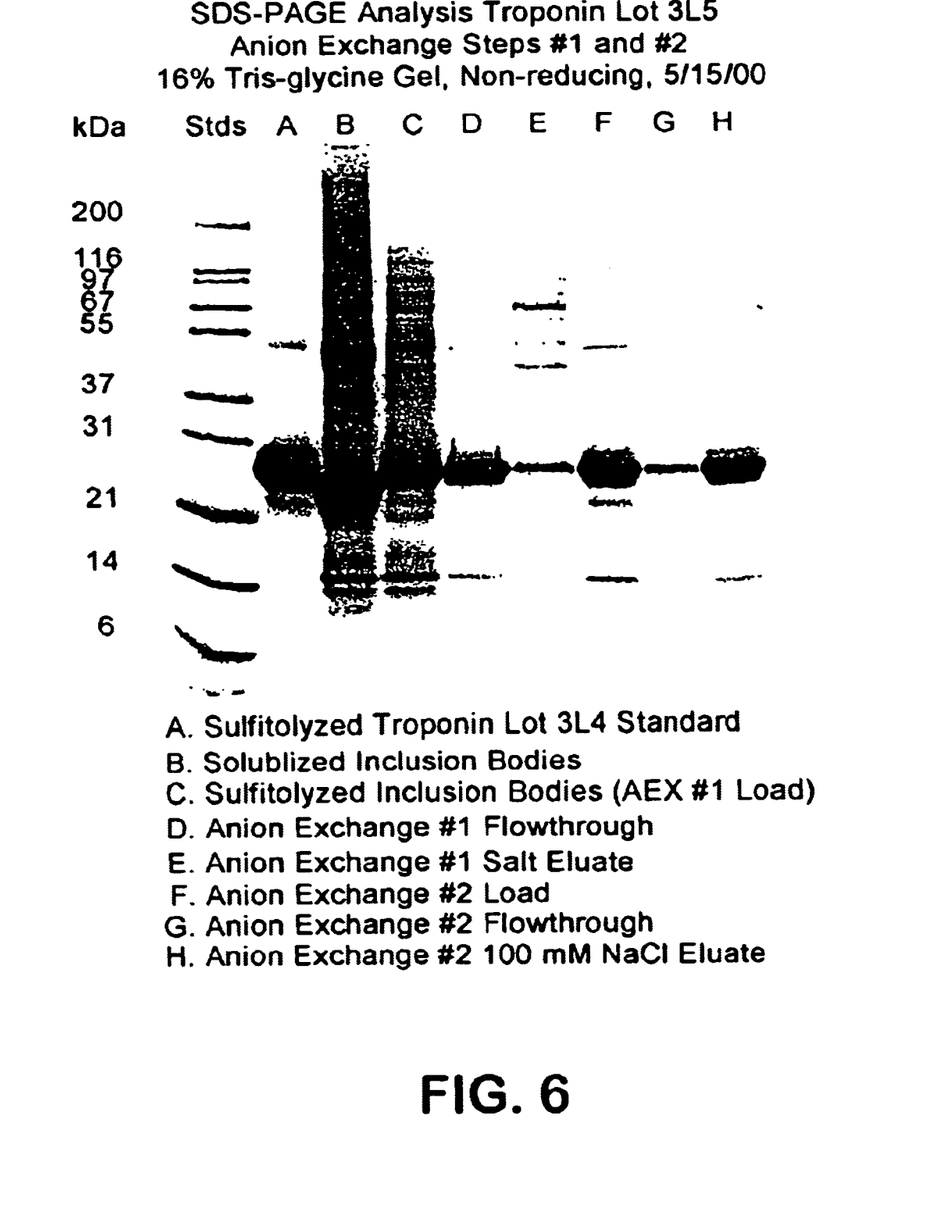
FIG. 6. SDS-PAGE analysis troponin lot after anion exchange steps no. 1 and no. 2 in 16% tris-glycine gel, under reducing conditions. A-H refer to lanes in the SDS-PAGE gel. A. Sulfitolyzed troponin Lot 3L4 standard; B. solubilized inclusion bodies; C. sulfitolyzed inclusion bodies (AEX No. 1 load); D. anion exchange no. 1 flowthrough; E. anion exchange no. 1 salt eulate; F. anion exchange no. 2 load; (3. anion exchange no. 2 flowthrough; and H. anion exchange no. 2 100 mM NaCl eluate.
Figure 7:
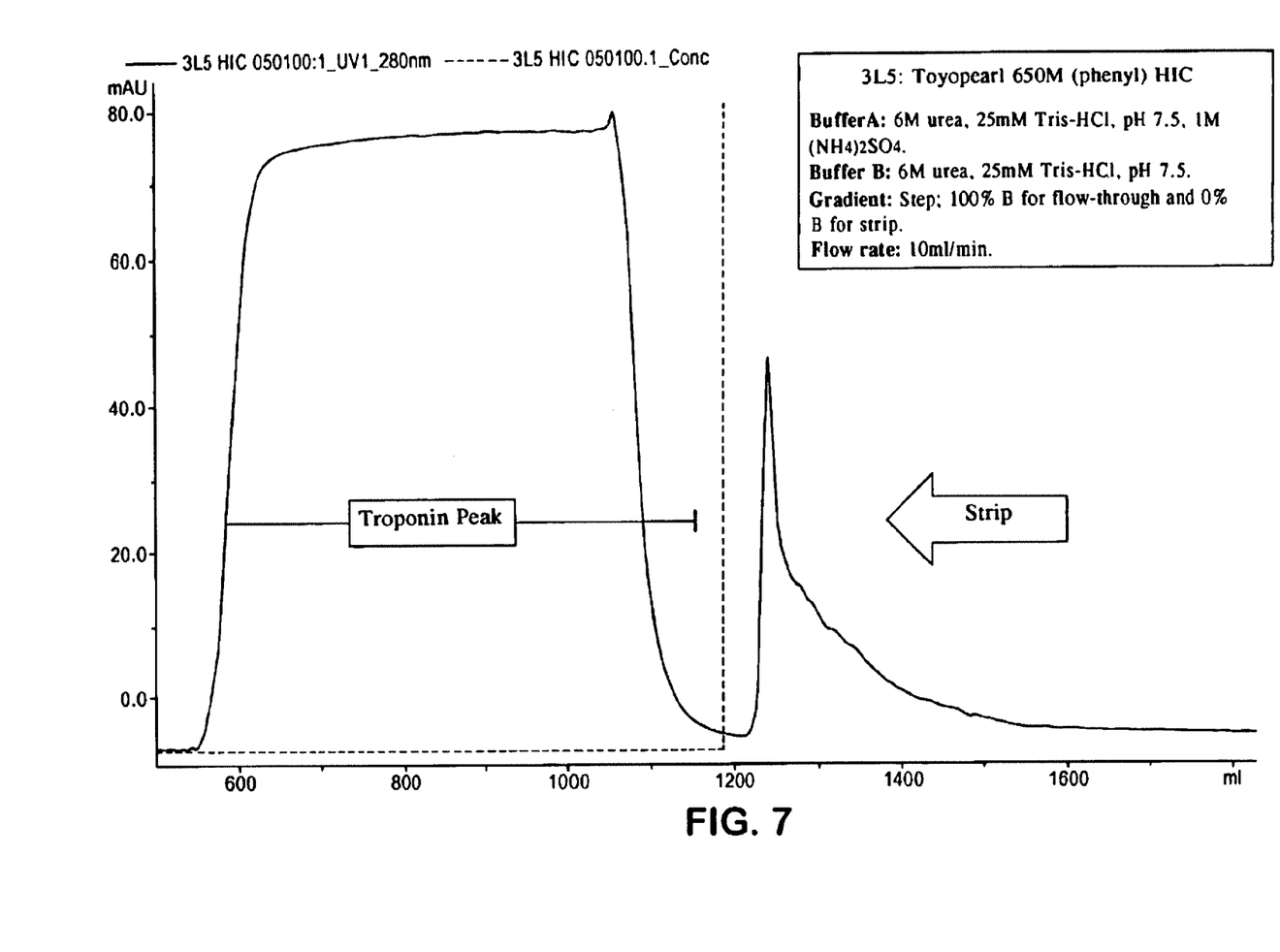
FIG. 7. Toyopearl 650M (phenyl) HIC chromatograph. Buffer A: 6M urea, 25 mM Tris-HCl, pH 7.5, 1M $(NH_4)_2SO_4$; Buffer B: 6M urea, 25 mM Tris-HCl, pH 7.5; Gradient: Step, 100% B for the flow-through and 0% B for strip; and Flow rate: 10 ml/min.
Figure 8:
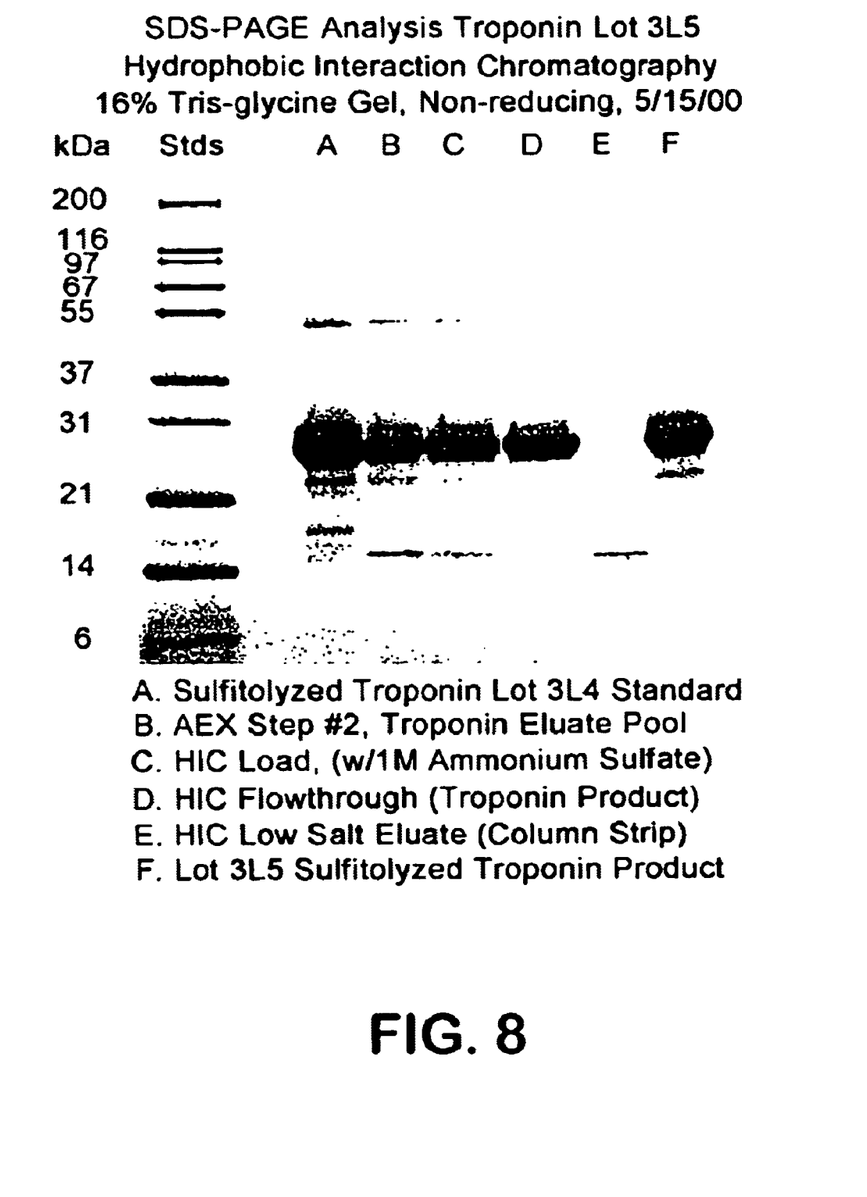
FIG. 8. SDS-PAGE analysis troponin lot after hydrophobic interaction chromatography in 16% tris-glycine gel, under non-reducing conditions. A-F refers to lanes in the SDS-PAGE gel. A. Sulfitolyzed troponin Lot 3L4 standard; B. AEX step no. 2, troponin eulate pool; C. HIC load (w/1M ammonium sulfate); D. HIC flowthrough (troponin product); E. HIC low salt eulate (column strip); F. lot 3L5 sulfitoylzed troponin product.

TnI Purification. Sulfitolyzed recombinant human TnI was purified by a five step process (FIG. 3). Solubilized, sulfitolyzed TnI-containing inclusion bodies (200 ml) were loaded onto a 3 liter volume Q-Sepharose FF (Pharmacia) column pre-equilibrated in 6M urea, 25 mM Tris, 0.1M NaCl pH 7.5 at 150 ml/minute (FIG. 4). The purified TnI was collected in the column flowthrough (approximately 3000 ml, total). The recovered TnI was concentrated and buffer exchanged by UF/DF using a 0.2 ft$^2$ Pall Omega cassette. Initial concentration was to 10× volume (300 ml) followed by diafiltration against 5 liters of 6M urea, 25 mM Tris pH 7.5. This material was loaded onto a 300 ml volume Q-Sepharose FF column pre-equilibrated in 6M urea, 25 mM Tris, pH 7.5 at 20 ml/minute. The bound TnI was eluted from the column by a step wash with 6M urea, 25 mM Tris, 80 mM NaCl pH 7.5 (FIGS. 5, 6). This eluted troponin (500 ml) was loaded onto a 60 ml column of Toyopearl 650M Phenyl HIC resin after addition of ammonium sulfate to a final concentration of 1M. The column was pre-equilibrated with 6M urea, 25 mM Tris, 1M ammonium sulfate pH 7.5. The purified troponin was collected as the unbound flowthrough from this column (FIGS. 7, 8), concentrated 2.5-fold and buffer exchanged for storage by UF/DF using a 0.2 ft$^2$ Pall Omega cartridge against 5 liters of 25 mM sodium citrate, 150 mM NaCl pH 3. Purified TnI was stored frozen at −70° C.

Figure 9:
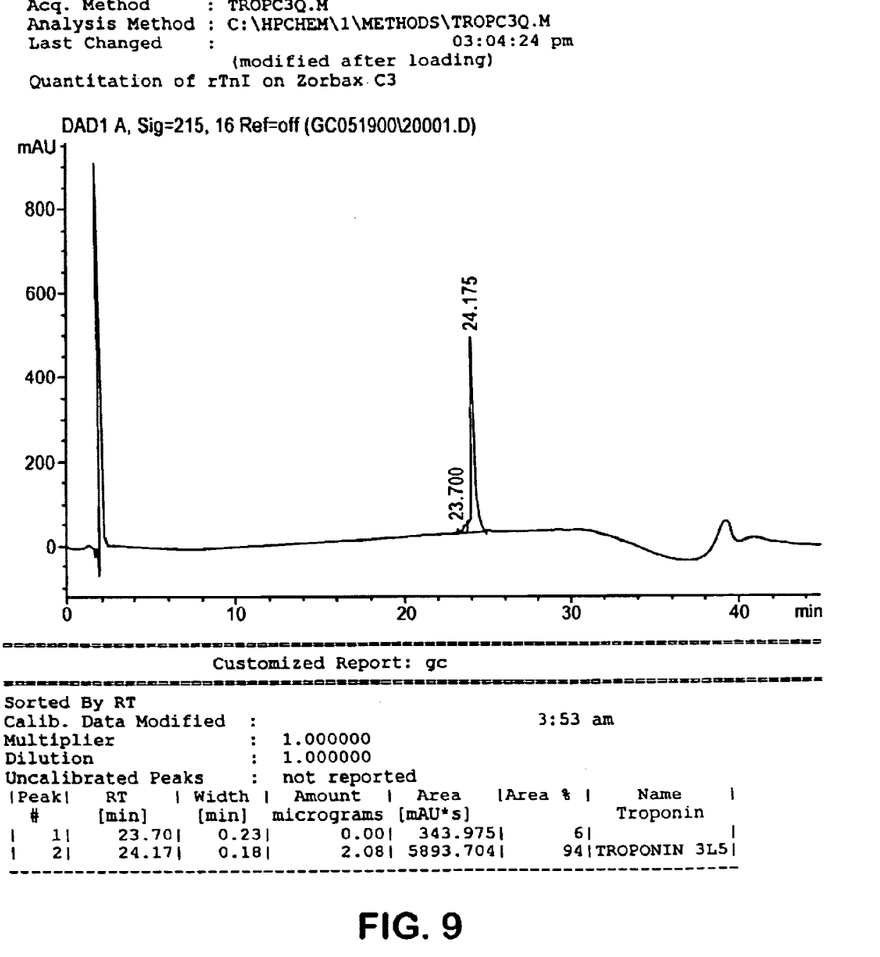
FIG. 9. Quantitation of rTnI on Zorbax C3.
Figure 10:
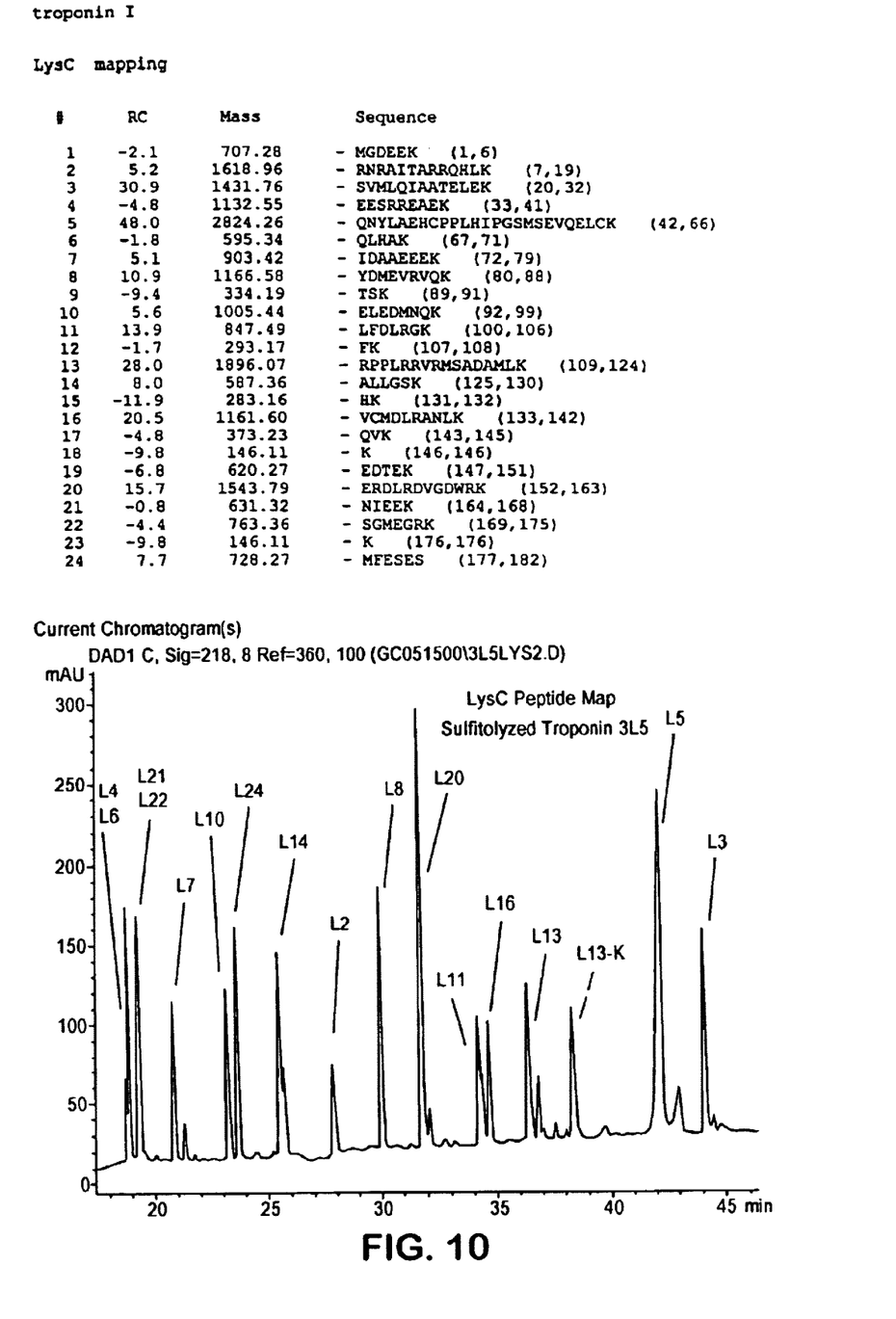
FIG. 10. Troponin I Lysate C mapping

Protein purity was determined by SDS-PAGE (FIG. 8) and reverse phase chromatography (FIG. 9) and protein identity was confirmed by peptide mapping with peptide mass and fragmentation analysis (FIG. 10). Yield determinations for each step in the process were determined by quantitative reverse phase chromatography. Residual DNA levels, measured by DNA Threshold, were less than or equal to 12 pg DNA/mg protein. Endotoxin testing of final product by LAL (gel-clot) indicated less than or equal to 3 endotoxin units (EU)/mg protein.

Figure 11:
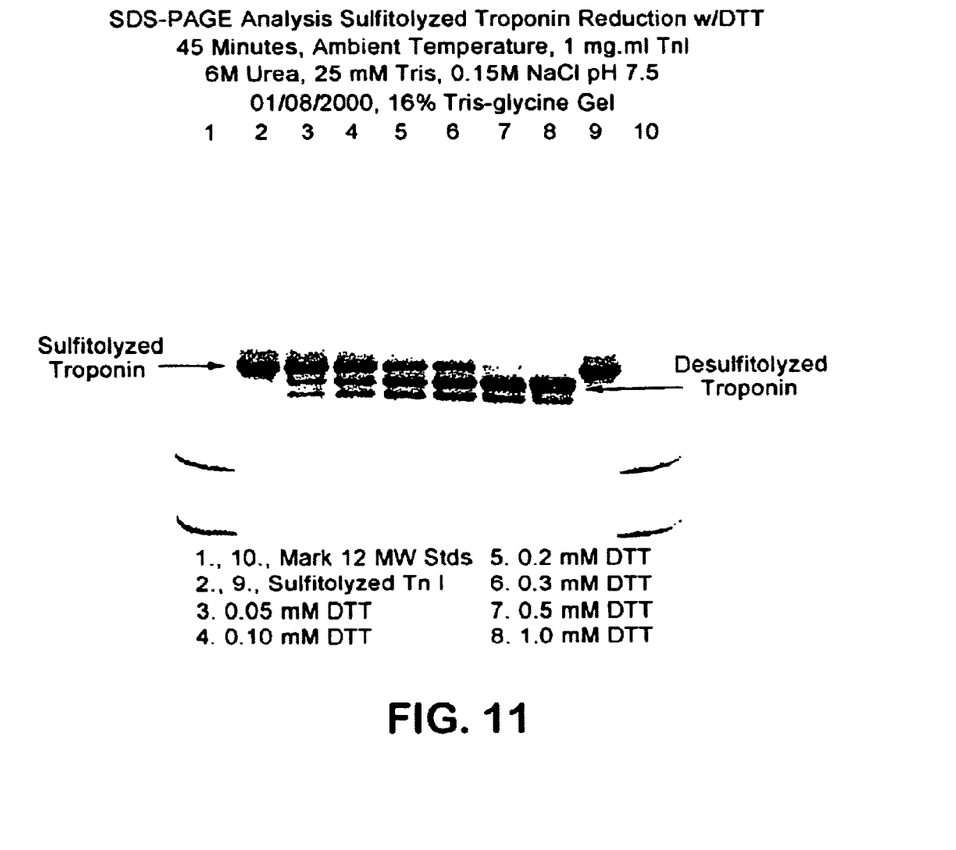
FIG. 11. SDS-PAGE analysis of sulfitolyzed troponin reduction with dithiothreitol for 45 mins. at ambient temperature. One mg/ml TnI and six M urea, 25 mM ti-is, 0.15 M NaCl ph 7.5, run on a 16% tris-glycine gel. 1,10., M 12 Molecular Weight Standards; 2. 9., sulfitolyzed TnI; 3.0.05 mM DTT; 4. 0.10 mM DTT; 5. 0.2 mM DTF; 6. 0.3 mM DTT; 7.0.5 mM DTT, 8. 1.0 mM DTT.

TnI Desulfitolyzation. For removal of sulfate groups from cysteine sidechains, purified TnI in sodium citrate storage buffer was first buffer exchanged by dialysis or diafiltration into 6M or 8M urea, 25 mM Tris, 0.15M NaCl pH 7.5. Desulfitolyzation was accomplished by addition of DTT to a final concentration of 0.1M and incubation at ambient temperature for 45 minutes to 1 hour. FIG. 11 shows the SDS-PAGE analysis of an experiment establishing the minimum conditions for desulfitolysis of recombinant human troponin I. For processing recombinant sulfitolyzed troponin I the level of reductant, concentration of urea and incubation time were increased over the minimum values established to insure complete conversion of the modified cysteine sidechains to the free sulfhydryl. The TnI solution was subsequently buffer exchanged by dialysis or diafiltration in the presence of reductant to a pH of 6 (8M urea, 10 mM sodium citrate, 5 mM DTT, 0.15M NaCl, pH 6), then into buffer minus reductant (8M urea, 10 mM sodium citrate, 0.15M NaCl, pH 6) to preclude the formation of intermolecular disulfides upon removal of reductant at high pH.

Analytical Methods. SDS-PAGE analysis was performed using Novex Pre-cast 16% Tris-glycine gels, sample and running buffers, and molecular weight markers. Gels were stained with Novex colloidal Coomassie blue stain.

Reverse phase chromatographic analyses were performed on an HP 1100 liquid chromatograph using a 2.1×150 mm Zorbax C3SB column run at a flowrate of 0.25 ml/minute at 25° C. Buffer for reverse phase column equilibration was 0.1% Trifluroacetic acid (TFA) in water. TnI samples were analyzed by gradient elution from 0.1% TFA/water to 0.1% TFA/acetonitrile at 1%/minute. Column eluates were monitored by on-line UV detection at 215 nm.

Peptide maps of TnI were generated by dilution of stock samples of TnI to 1 mg/ml with 0.1M Tris buffer, pH 8, followed by digestion with a 1:20 enzyme:substrate ratio of endoproteinase LysC at 37° C. for 6 hours. LysC peptide fragments were resolved by reverse phase chromatography on a 2.1×150 mm Zorbax C18SB column using a gradient of 0.1% TFA/water to 0.1% TFA/acetonitrile at 0.25 ml/minute. Eluted peptide fragments of TnI were identified by on-line LC/MS detection using a Finnigan LCQ ion trap mass spectrometer set to perform automated peptide detection/fragmentation analysis.

Protein concentration analysis was performed using reverse phase analysis of TnI on the Zorbax C3SB column, whose linear detection limits were calibrated for quantitation using a TnI standard whose concentration was determined by UV 280 nm measurement and the application of the Beer/Lambert equation (A=Ebc) with an extinction coefficient of 0.4.

Residual DNA analysis was performed with DNA Threshold. Endotoxin contaminant was measured by Limulus Amoebocyte Lysate (LAL) gel-clot test.

Results

Samples were removed at each process step for analysis. Sample quantities were determined by reverse phase chromatography. The troponin peak absorbance at 215 nm was measured for each sample in replicate, averaged, and the quantity of protein calculated using a reverse phase calibration curve based upon a standard troponin dilution series. The calibrant standard concentration was determined using the Beer/Lambert equation, the standard absorbance at 280 nm, and an extinction coefficient of 0.4.

During final ultrafiltration/diafiltration processing, product precipitation was noted. After removing final products residual troponin precipitate in the UF/DF was resolubilized by washing with 15 mL of 6 M urea, 10 mM of sodium citrate, 0.15 m NaCl, ph 6. This resolubilzed troponin was buffer exchanged to remove urea and analyzed for troponin. The product total is the sum of the troponin recovered during the final UF/DF step and the resolubilzed, buffer exchange cassette wash.

Data Summary Table
Lot 3L5 Sulfitolyzed Tropinin Purification

| SAMPLE | VOLUME (ML) | CONCENTRATION MG/ML | AMOUNT | RECOVERY % |
|---|---|---|---|---|
| Cell Pellet | — | — | 148 grams | — |
| Inclusion Body Final Pellet | — | — | 10.48 grams | — |
| Q1 Load, Sulfitolyzed Inclusion Bodies | 250 | 2.56 | 640 mg | 100 |
| Q1 Flowthrough | 3000 | 0.21 | 644 mg | 100 |
| Q1 UF | 300 | 1.94 | 582 mg | 91 |
| Q1 DF | 290 | 1.99 | 577 mg | 90 |
| Q2 Bound, 80 mM NaCl Eulate | 500 | 0.98 | 489 mg | 76 |
| HIC Load, 1 M Ammonium Sulfate | 500 | 0.99 | 499 mg | 78 |
| HIC Flowthrough | 550 | 0.87 | 479 mg | 75 |
| Final UF/DF | 200 | 1.60 | 318 mg | 50 |
| Cassette Wash/ Reprocessed Precipitate | 50 | 0.69 | 34 mg | 5 |
| Product Total | — | — | 352 mg | 55 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, patent applications, publications, procedures, and other materials cited herein are hereby incorporated by reference in their entireties.

What is claimed is:

1. A method of preparing naturally occurring Troponin I for purification, which method comprises protecting free sulfhydryl groups of Troponin I under reducing conditions, wherein the free sulfhydryl groups are protected by sulfitolyzation.

2. The method according to claim 1, wherein sulfitolyzation comprises reacting Troponin I with sodium sulfite.

3. The method according to claim 1, wherein the Troponin I is expressed in a bacterial expression system.

4. The method according to claim 3, wherein the bacterial expression system is an E. coil expression system.

5. The method according to claim 1, which further comprises purifying the sulfhydryl group protected Troponin I.

6. The method according to claim 5, wherein the Troponin I is purified by chromatography.

7. The method according to claim 5, which comprises purifying the Troponin I under non-reducing conditions.

8. The method according to claim 5, which further comprises deprotecting the sulfhydryl groups from the purified Troponin I.

9. A method of purifying naturally occurring Troponin I, which method comprises subjecting Troponin I comprising sulfhydryl protecting groups to chromatography to purify the sulfhydryl group protected Troponin I.

10. The method according to claim 9, wherein the sulfhydryl groups are protected by sulfitolization.

11. The method according to claim 10, wherein sulfitolyzation comprises reacting, denatured Troponin I with sodium sulfite.

12. The method according to claim 10, which comprises subjecting the Troponin I to chromatography under non-reducing conditions.

13. The method according to claim 9, wherein the Troponin I is expressed in a bacterial expression system.

14. The method according to claim 13, wherein the bacterial expression system is an E. coli expression system.

15. The method according to claim 9, wherein the Chromatography is an anion exchange.

16. The method according to claim 15, wherein the chromatography is hydrophobic interaction.

* * * * *